United States Patent
Thorsteinsdottir et al.

(10) Patent No.: US 9,895,250 B2
(45) Date of Patent: Feb. 20, 2018

(54) ORTHOPEDIC DEVICE AND METHOD FOR SECURING THE SAME

(71) Applicant: OSSUR HF, Reykjavik (IS)

(72) Inventors: Hildur Inga Thorsteinsdottir, Reykjavik (IS); Arni Thor Ingimundarson, Reykjavik (IS); Helga Run Palsdottir, Reykjavik (IS); Bjorn Omarsson, Reykjavik (IS)

(73) Assignee: OSSUR HF, Reykjavik (IS)

( * ) Notice: Subject to any disclaimer, the term of this patent is extended or adjusted under 35 U.S.C. 154(b) by 0 days.

(21) Appl. No.: 15/147,192

(22) Filed: May 5, 2016

(65) Prior Publication Data

US 2016/0242945 A1 Aug. 25, 2016

Related U.S. Application Data

(63) Continuation of application No. 14/148,881, filed on Jan. 7, 2014, now Pat. No. 9,358,146.
(Continued)

(51) Int. Cl.
*A61F 5/01* (2006.01)

(52) U.S. Cl.
CPC .......... *A61F 5/0109* (2013.01); *A61F 5/0102* (2013.01); *A61F 5/0106* (2013.01);
(Continued)

(58) Field of Classification Search
CPC .. A61F 5/00; A61F 5/01; A61F 5/0102; A61F 5/0106; A61F 5/0109; A61F 5/0111; A61F 5/0118; A61F 5/0123; A61F 5/0127; A61F 5/013; A61F 5/01; A61F 5/0193; A61F 2005/0139; A61F 5/0125; A61F 2005/0137; A61F 2005/0167; A61F 2005/0179; A61F 2005/0197; A61F 2005/0174; A61F 2005/0181; A61F 2250/001; A61F 5/022; A61F 2/68; A61F 2002/701; A61F 2002/745; A61H 3/00; A61H 1/024; A61H 1/0244; A61H 1/0266
(Continued)

(56) References Cited

U.S. PATENT DOCUMENTS

| 667,768 A | 2/1901 | Puy |
| 777,585 A | 12/1904 | Beatty |

(Continued)

FOREIGN PATENT DOCUMENTS

| CN | 101128169 A | 2/2008 |
| DE | 846 895 C | 8/1952 |

(Continued)

OTHER PUBLICATIONS

International Search Report from PCT Application No. PCT/US2016/012346, dated May 6, 2016.
(Continued)

*Primary Examiner* — Keri J Nelson
(74) *Attorney, Agent, or Firm* — Workman Nydegger (57) ABSTRACT

An orthopedic device has various frame elements concealed by a sleeve defining pockets into which such frame elements are located. The orthopedic device includes a strap tightening assembly adapted to secure a plurality of straps simultaneously. The frame may include flexible edge features located along a periphery thereof.

16 Claims, 6 Drawing Sheets

Related U.S. Application Data (60) Provisional application No. 61/904,010, filed on Nov. 14, 2013, provisional application No. 61/749,578, filed on Jan. 7, 2013.

(52) U.S. Cl.
CPC ............ *A61F 5/0123* (2013.01); *A61F 5/013* (2013.01); *A61F 5/0111* (2013.01); *A61F 5/0118* (2013.01); *A61F 5/0127* (2013.01)

(58) Field of Classification Search
USPC ................................ 602/16, 20–28; 128/882
See application file for complete search history.

(56) References Cited

U.S. PATENT DOCUMENTS

| | | |
|---|---|---|
| 937,478 A | 10/1909 | Sims |
| 1,153,334 A | 9/1915 | Oswald |
| 1,227,700 A | 5/1917 | Tucker |
| 1,328,541 A | 1/1920 | Palmer |
| 1,510,408 A | 9/1924 | Lychou |
| 1,622,211 A | 3/1927 | Sheehan |
| 2,032,923 A | 3/1936 | Eldridge |
| 2,179,903 A | 11/1939 | Spears |
| 2,467,907 A | 4/1949 | Peckham |
| 2,573,866 A | 11/1951 | Murphy |
| 2,717,841 A | 9/1955 | Biefeld et al. |
| 2,935,065 A | 5/1960 | Homier et al. |
| 3,031,730 A | 5/1962 | Morin |
| 3,046,981 A | 7/1962 | Biggs, Jr. et al. |
| 3,089,486 A | 5/1963 | Pike |
| 3,266,113 A | 8/1966 | Flanagan, Jr. |
| 3,463,147 A | 8/1969 | Stubbs |
| 3,514,313 A | 5/1970 | Martel et al. |
| 3,520,765 A | 7/1970 | Bateman |
| 3,528,412 A | 9/1970 | McDavid |
| 3,581,741 A | 1/1971 | Rosman |
| 3,561,436 A | 2/1971 | Gaylord, Jr. |
| 3,594,863 A | 7/1971 | Erb |
| 3,594,865 A | 7/1971 | Erb |
| 3,742,557 A | 7/1973 | Francois |
| 3,752,619 A | 8/1973 | Menzin et al. |
| 3,758,657 A | 9/1973 | Menzin et al. |
| 3,789,842 A | 2/1974 | Froimson |
| 3,804,084 A | 4/1974 | Lehman |
| 3,817,244 A | 6/1974 | Taylor |
| 3,851,357 A | 12/1974 | Ribich et al. |
| 3,877,426 A | 4/1975 | Nirschl |
| 3,916,077 A | 10/1975 | Damrau |
| 3,927,881 A | 12/1975 | Lemelson et al. |
| 3,945,046 A | 3/1976 | Stromgren |
| 3,955,565 A | 5/1976 | Johnson, Jr. |
| 4,193,395 A | 3/1980 | Gruber |
| 4,204,532 A | 5/1980 | Lind et al. |
| 4,240,414 A | 12/1980 | Theisler |
| 4,269,179 A | 5/1981 | Burton et al. |
| 4,269,181 A | 5/1981 | Delannoy |
| 4,275,716 A | 6/1981 | Scott, Jr. |
| 4,280,489 A | 7/1981 | Johnson, Jr. |
| 4,291,072 A | 9/1981 | Barrett et al. |
| 4,296,744 A | 10/1981 | Palumbo |
| 4,304,560 A | 12/1981 | Greenwood |
| 4,336,279 A | 6/1982 | Metzger |
| 4,372,298 A | 2/1983 | Lerman |
| 4,381,768 A | 5/1983 | Erichsen et al. |
| 4,386,723 A | 6/1983 | Mule |
| 4,396,012 A | 8/1983 | Cobiski |
| 4,470,857 A | 9/1984 | Casalou |
| 4,472,461 A | 9/1984 | Johnson |
| 4,506,661 A | 3/1985 | Foster |
| 4,528,440 A | 7/1985 | Ishihara |
| 4,554,913 A | 11/1985 | Womack et al. |
| 4,572,170 A | 2/1986 | Cronk et al. |
| 4,617,214 A | 10/1986 | Billarant |
| 4,632,098 A | 12/1986 | Grundei et al. |
| 4,677,713 A | 7/1987 | Copp |
| 4,693,921 A | 9/1987 | Billarant et al. |
| D292,529 S | 10/1987 | Saare |
| 4,697,583 A | 10/1987 | Mason et al. |
| 4,724,831 A | 2/1988 | Huntjens |
| 4,768,500 A | 9/1988 | Mason et al. |
| 4,775,310 A | 10/1988 | Fischer |
| D298,568 S | 11/1988 | Womack et al. |
| 4,782,605 A | 11/1988 | Cahpnick |
| 4,791,916 A | 12/1988 | Paez |
| 4,794,028 A | 12/1988 | Fischer |
| 4,801,138 A | 1/1989 | Airy et al. |
| 4,802,939 A | 2/1989 | Billarant et al. |
| 4,805,606 A | 2/1989 | McDavid, III |
| 4,854,308 A | 8/1989 | Drillio |
| 4,856,501 A | 8/1989 | Castillo et al. |
| 4,856,502 A | 8/1989 | Ersfeld et al. |
| 4,872,243 A | 10/1989 | Fischer |
| 4,922,929 A | 5/1990 | DeJournett |
| 4,933,035 A | 6/1990 | Billarant et al. |
| 4,953,543 A | 9/1990 | Grim et al. |
| 4,961,544 A | 10/1990 | Bidoia |
| 4,966,133 A | 10/1990 | Kausek |
| 4,989,593 A | 2/1991 | Campagna et al. |
| 4,991,574 A | 2/1991 | Pocknell |
| 4,991,640 A | 2/1991 | Verkindt et al. |
| 5,002,045 A * | 3/1991 | Spademan ............ A61F 5/0125 602/16 |
| 5,005,527 A | 4/1991 | Hatfield |
| 5,016,621 A | 5/1991 | Bender |
| 5,018,514 A | 5/1991 | Grood et al. |
| 5,020,196 A | 6/1991 | Panach et al. |
| 5,022,109 A | 6/1991 | Pekar |
| 5,063,916 A | 11/1991 | France et al. |
| 5,067,772 A | 11/1991 | Koa |
| 5,077,870 A | 1/1992 | Melbye et al. |
| 5,085,210 A | 2/1992 | Smith, III |
| 5,112,296 A | 5/1992 | Beard et al. |
| 5,152,038 A * | 10/1992 | Schoch .................. A43C 11/16 24/68 SK |
| 5,154,682 A | 10/1992 | Kellerman |
| 5,157,813 A | 10/1992 | Carroll |
| 5,181,331 A | 1/1993 | Berger |
| 5,227,698 A | 7/1993 | Simpson et al. |
| 5,242,379 A | 9/1993 | Harris et al. |
| 5,267,951 A | 12/1993 | Ishii |
| 5,277,697 A | 1/1994 | France et al. |
| 5,277,698 A | 1/1994 | Taylor |
| 5,288,287 A | 2/1994 | Castillo et al. |
| 5,302,169 A | 4/1994 | Taylor |
| 5,314,455 A | 5/1994 | Johnson, Jr. et al. |
| 5,316,547 A | 5/1994 | Gildersleeve |
| 5,322,729 A | 6/1994 | Heeter et al. |
| 5,334,135 A | 8/1994 | Grim et al. |
| 5,344,135 A | 9/1994 | Isobe et al. |
| 5,368,549 A | 11/1994 | McVicker |
| 5,383,845 A | 1/1995 | Nebolon |
| 5,397,296 A | 3/1995 | Sydor et al. |
| 5,415,625 A | 5/1995 | Cassford |
| 5,431,623 A | 7/1995 | Rice |
| 5,437,619 A | 8/1995 | Malewicz et al. |
| 5,445,602 A | 8/1995 | Grim et al. |
| 5,449,341 A | 9/1995 | Harris |
| 5,458,565 A | 10/1995 | Tillinghast, III |
| 5,468,219 A | 11/1995 | Crippen |
| 5,472,413 A | 12/1995 | Detty |
| 5,474,524 A | 12/1995 | Carey |
| 5,497,513 A | 3/1996 | Arabeyre et al. |
| 5,500,268 A | 3/1996 | Billarant |
| 5,512,039 A | 4/1996 | White |
| 5,513,658 A | 5/1996 | Goseki |
| 5,514,081 A | 5/1996 | Mann |
| 5,527,269 A | 6/1996 | Reithofer |
| 5,540,982 A | 7/1996 | Scholz et al. |
| 5,542,911 A | 8/1996 | Cassford et al. |
| 5,562,605 A | 10/1996 | Taylor |
| 5,599,288 A | 2/1997 | Shirley et al. |
| 5,695,452 A | 2/1997 | Grim et al. |

(56) References Cited

U.S. PATENT DOCUMENTS

| | | | |
|---|---|---|---|
| 5,614,045 A | 3/1997 | Billarant | |
| 5,635,201 A | 6/1997 | Fabo | |
| 5,638,588 A | 6/1997 | Jungkind | |
| 5,654,070 A | 8/1997 | Billarant | |
| 5,656,226 A | 8/1997 | McVicker | |
| 5,665,449 A | 9/1997 | Billarant | |
| 5,685,830 A * | 11/1997 | Bonutti | A61F 5/013 601/33 |
| 5,713,837 A | 2/1998 | Grim et al. | |
| D392,877 S | 3/1998 | Eguchi | |
| 5,737,854 A | 4/1998 | Sussmann | |
| 5,759,167 A | 6/1998 | Shields, Jr. et al. | |
| 5,769,808 A | 6/1998 | Matthijs et al. | |
| 5,774,902 A | 7/1998 | Gehse | |
| 5,795,640 A | 8/1998 | Billarant | |
| 5,807,294 A | 9/1998 | Cawley et al. | |
| 5,823,981 A | 10/1998 | Grim et al. | |
| 5,840,398 A | 11/1998 | Billarant | |
| 5,857,988 A * | 1/1999 | Shirley | A61F 5/0125 602/16 |
| 5,857,989 A | 1/1999 | Smith, III | |
| 5,865,776 A | 2/1999 | Springs | |
| 5,865,777 A | 2/1999 | Detty | |
| 5,865,782 A | 2/1999 | Fareed | |
| 5,873,848 A | 2/1999 | Fulkerson | |
| 5,891,061 A | 4/1999 | Kaiser | |
| 5,900,303 A | 5/1999 | Billarant | |
| 5,916,187 A | 6/1999 | Brill | |
| 5,948,707 A | 9/1999 | Crawley et al. | |
| 5,971,946 A | 10/1999 | Quinn | |
| 6,010,474 A | 1/2000 | Wycoki | |
| 6,021,780 A | 2/2000 | Darby | |
| 6,022,617 A | 2/2000 | Calkins | |
| 6,024,712 A | 2/2000 | Iglesiasa et al. | |
| 6,063,048 A | 5/2000 | Bodenschatz et al. | |
| 6,110,138 A | 8/2000 | Shirley | |
| 6,111,138 A | 8/2000 | Van Wijck et al. | |
| 6,142,965 A | 11/2000 | Mathewson | |
| 6,152,893 A | 11/2000 | Pigg et al. | |
| 6,159,583 A | 12/2000 | Calkins | |
| 6,250,651 B1 | 6/2001 | Reuss et al. | |
| 6,254,554 B1 | 7/2001 | Turtzo | |
| 6,267,741 B1 | 7/2001 | Lerman | |
| RE37,338 E | 8/2001 | McVicker | |
| 6,287,268 B1 | 9/2001 | Gilmour | |
| 6,289,558 B1 | 9/2001 | Hammerslag | |
| 6,360,404 B1 | 3/2002 | Mudge et al. | |
| 6,368,295 B1 | 4/2002 | Lerman | |
| 6,402,713 B1 | 6/2002 | Doyle | |
| 6,405,731 B1 | 6/2002 | Ching | |
| 6,413,232 B1 | 7/2002 | Townsend et al. | |
| 6,416,074 B1 | 7/2002 | Maravetz et al. | |
| 6,461,318 B2 | 10/2002 | Freeman et al. | |
| 6,485,776 B2 | 11/2002 | Janusson et al. | |
| 6,520,926 B2 | 2/2003 | Hall | |
| 6,540,703 B1 | 4/2003 | Lerman | |
| 6,540,709 B1 | 4/2003 | Smits | |
| D477,409 S | 7/2003 | Mills et al. | |
| 6,592,538 B1 | 7/2003 | Hotchkiss et al. | |
| 6,592,539 B1 | 7/2003 | Einarsson et al. | |
| 6,596,371 B1 | 7/2003 | Billarant et al. | |
| 6,598,250 B1 | 7/2003 | Pekar | |
| 6,543,158 B2 | 8/2003 | Dieckhaus | |
| 6,656,142 B1 | 12/2003 | Lee | |
| 6,666,894 B2 | 12/2003 | Perkins et al. | |
| 6,689,080 B2 | 2/2004 | Castillo | |
| 6,726,641 B2 | 4/2004 | Chiang et al. | |
| 6,735,819 B2 | 5/2004 | Iverson et al. | |
| 6,769,155 B2 | 8/2004 | Hess et al. | |
| 6,773,411 B1 | 8/2004 | Alvarez | |
| 6,861,371 B2 | 3/2005 | Kamikawa et al. | |
| 6,861,379 B1 | 3/2005 | Blaszcykiewicz | |
| 6,898,804 B2 | 5/2005 | Sandler | |
| 6,898,826 B2 | 5/2005 | Draper et al. | |
| 6,936,020 B2 | 8/2005 | Davis | |
| D519,637 S | 4/2006 | Nordt et al. | |
| D519,638 S | 4/2006 | Nordt et al. | |
| 7,025,738 B2 | 4/2006 | Hall | |
| D520,141 S | 5/2006 | Nordt et al. | |
| D521,644 S | 5/2006 | Nordt et al. | |
| 7,037,287 B2 | 5/2006 | Cormier et al. | |
| 7,150,721 B2 | 12/2006 | Houser | |
| 7,161,056 B2 | 1/2007 | Gudnason et al. | |
| 7,169,720 B2 | 1/2007 | Etchells et al. | |
| 7,198,610 B2 | 4/2007 | Ingimundarson et al. | |
| 7,303,539 B2 | 12/2007 | Binder et al. | |
| 7,367,958 B2 | 5/2008 | McBean et al. | |
| 7,448,115 B2 | 11/2008 | Howell et al. | |
| 7,762,973 B2 | 7/2010 | Einarsson et al. | |
| 7,806,842 B2 * | 10/2010 | Stevenson | A61F 5/0125 602/16 |
| 7,874,996 B2 | 1/2011 | Weinstein et al. | |
| 7,905,851 B1 | 3/2011 | Bledsoe | |
| 7,937,973 B2 | 5/2011 | Sorensen et al. | |
| 8,328,747 B2 | 12/2012 | Matsunaga | |
| 2001/0020143 A1 | 9/2001 | Stark et al. | |
| 2001/0056251 A1 | 12/2001 | Peters | |
| 2002/0032397 A1 | 3/2002 | Coligado | |
| 2002/0077574 A1 | 6/2002 | Gildersleeve et al. | |
| 2002/0082542 A1 | 6/2002 | Hall | |
| 2002/0095750 A1 | 7/2002 | Hammerslag | |
| 2002/0132086 A1 | 9/2002 | Su-Tuan | |
| 2003/0032907 A1 | 2/2003 | Prahl | |
| 2003/0069531 A1 | 4/2003 | Hall | |
| 2003/0204156 A1 | 10/2003 | Nelson et al. | |
| 2004/0002674 A1 | 1/2004 | Sterling | |
| 2004/0054311 A1 | 2/2004 | Sterling | |
| 2004/0058102 A1 | 3/2004 | Baychar | |
| 2004/0137178 A1 | 7/2004 | Janusson et al. | |
| 2004/0137192 A1 | 7/2004 | McVicker | |
| 2004/0153016 A1 | 8/2004 | Salmon et al. | |
| 2004/0176715 A1 | 9/2004 | Nelson | |
| 2004/0199095 A1 | 10/2004 | Frangi | |
| 2004/0225245 A1 | 11/2004 | Nelson | |
| 2004/0267179 A1 | 12/2004 | Lerman | |
| 2005/0020951 A1 | 1/2005 | Gaylord et al. | |
| 2005/0038367 A1 | 2/2005 | McCormick et al. | |
| 2005/0081339 A1 | 4/2005 | Sakabayashi | |
| 2005/0159691 A1 | 7/2005 | Turrini et al. | |
| 2005/0160627 A1 | 7/2005 | Dalgaard et al. | |
| 2005/0273025 A1 * | 12/2005 | Houser | A61F 5/0123 602/16 |
| 2006/0015980 A1 | 1/2006 | Nordt, III et al. | |
| 2006/0020237 A1 | 1/2006 | Nordt, III et al. | |
| 2006/0026732 A1 | 2/2006 | Nordt, III et al. | |
| 2006/0026733 A1 | 2/2006 | Nordt, III et al. | |
| 2006/0026736 A1 | 2/2006 | Nordt, III et al. | |
| 2006/0030802 A1 | 2/2006 | Nordt, III et al. | |
| 2006/0030803 A1 | 2/2006 | Nordt, III et al. | |
| 2006/0030804 A1 | 2/2006 | Nordt, III et al. | |
| 2006/0030805 A1 | 2/2006 | Nordt, III et al. | |
| 2006/0030806 A1 | 2/2006 | Nordt, III et al. | |
| 2006/0070164 A1 | 4/2006 | Nordt, III et al. | |
| 2006/0070165 A1 | 4/2006 | Nordt, III et al. | |
| 2006/0084899 A1 | 4/2006 | Verkade et al. | |
| 2006/0090806 A1 | 5/2006 | Friedline et al. | |
| 2006/0116619 A1 | 6/2006 | Weinstein et al. | |
| 2006/0135902 A1 | 6/2006 | Ingimundarson et al. | |
| 2006/0135903 A1 | 6/2006 | Ingimundarson et al. | |
| 2006/0155229 A1 | 7/2006 | Ceriani et al. | |
| 2006/0156517 A1 * | 7/2006 | Hammerslag | A43B 5/16 24/68 SK |
| 2006/0191110 A1 | 8/2006 | Howell et al. | |
| 2007/0083136 A1 | 4/2007 | Einarsson | |
| 2007/0130665 A1 | 6/2007 | Wang | |
| 2007/0167892 A1 | 7/2007 | Gramza et al. | |
| 2007/0167895 A1 | 7/2007 | Gramaza et al. | |
| 2007/0185425 A1 | 8/2007 | Einarsson et al. | |
| 2007/0225824 A1 | 9/2007 | Einarsson | |
| 2008/0034459 A1 | 2/2008 | Nordt, III et al. | |
| 2008/0066272 A1 * | 3/2008 | Hammerslag | A43C 11/14 24/712 |
| 2008/0229556 A1 | 9/2008 | Hammer | |
| 2009/0099562 A1 | 4/2009 | Ingimundarson et al. | |

(56) References Cited

U.S. PATENT DOCUMENTS

| | | |
|---|---|---|
| 2009/0126413 A1 | 5/2009 | Sorensen et al. |
| 2010/0068464 A1 | 3/2010 | Meyer |
| 2010/0125231 A1 | 5/2010 | Knecht |
| 2011/0057466 A1 | 3/2011 | Sachee et al. |
| 2011/0275970 A1 | 11/2011 | Paulos et al. |
| 2012/0010547 A1 | 1/2012 | Hinds |
| 2012/0046585 A1 | 2/2012 | Lee et al. |
| 2012/0090624 A1 | 4/2012 | Chang |
| 2012/0109031 A1 | 5/2012 | Vollbrecht et al. |
| 2012/0220910 A1 | 8/2012 | Gaylord et al. |
| 2014/0121579 A1 | 5/2014 | Hinds |
| 2014/0194801 A1 | 7/2014 | Ingimundarson et al. |
| 2014/0214016 A1 | 7/2014 | Ingimundarson et al. |

FOREIGN PATENT DOCUMENTS

| | | |
|---|---|---|
| DE | 100 04 561 A1 | 8/2001 |
| DE | 20 2004 012 892 U1 | 10/2004 |
| EP | 0 050 769 A1 | 5/1985 |
| EP | 0 196 204 A2 | 10/1986 |
| EP | 0 611 069 A | 8/1994 |
| EP | 1016351 A1 | 7/2000 |
| EP | 2612626 A2 | 7/2013 |
| FR | 2 399 811 A1 | 3/1979 |
| FR | 2 553 996 A1 | 5/1985 |
| FR | 2 766 359 A1 | 1/1999 |
| GB | 1209413 A | 10/1970 |
| GB | 2 136 294 A | 9/1984 |
| GB | 2 455 972 A | 7/2009 |
| WO | 88/01855 A1 | 3/1988 |
| WO | 94/00082 A1 | 1/1994 |
| WO | 00/49982 A1 | 8/2000 |
| WO | 00/70984 A1 | 11/2000 |
| WO | 2006/015599 A1 | 2/2006 |
| WO | 2006/069221 A2 | 6/2006 |
| WO | 2006/069222 A2 | 6/2006 |
| WO | 2008/115376 A1 | 9/2008 |
| WO | 2009052031 A1 | 4/2009 |
| WO | 2010/117749 A2 | 10/2010 |
| WO | 2011/073803 A2 | 6/2011 |

OTHER PUBLICATIONS

Article: "An Orthosis for Medial or Lateral Stabilization of Arthritic Knees", by S. Cousins and James Foort, Orthotics and Prosthetics, vol. 29, No. 4, pp. 21-26, Dec. 1975.
Advertising Brochure: "NUKO Camp", 6 pages, Camp International, Inc. Jackson, MI (1984).
Advertising Brochure: "Lerman Multi-Ligaments Knee Control Orthosis", 2 pages, Zinco Industries, Inc. of Montrose, CA (1985).
"Information on Flexible Polyurethane Foam", in Touch, vol. 4, No. 3, Jul. 1994, 5 pages.
Advertisement: "Custom Engineered Fabrics and Products for Advanced High Performance", 1 page, Gehring Textiles (visited Dec. 15, 2005), http://www.gehringtextiles.com/d3.html.
Article: "Osteoarthritis of the Knee: An Information Booklet", Arthritis Research Campaign (visited Dec. 14, 2004) http://www.arc.org.uk/about_arth/booklets/6027/6027.htm.
Advertising Brochure: "Freedom to Perform-Fusion", 5 pages, (2005).
Advertising Brochure: "Fusion", 6 pages, Breg, Inc. of Vista, CA (2005).
Advertising Brochure: "Fusion XT", 2 pages, Breg, Inc. of Vista, CA (2005).
Advertising Brochure: "Anderson Knee Stabler", 4 pages, Omni Scientific, Inc. of Lafayette, CA. Feb. 7, 2013.
Advertising Brochure: "OTI Brace", 4 pages, Orthopedic Technology, Inc. of San Leandro, CA. Feb. 7, 2013.
Advertising Brochure: "The Four Axioms of Functional Bracing", 2 pages, Bledsoe by Medical Technology, Inc. (2005).
Advertising Brochure: "The Leader in Knee Motion Management," 8 pages. Donjoy, Carsbad, CA. Feb. 7, 2013.
Advertising Brochure: "The Lenox Hill Lightweight", 1page, Lenox Hill Brace, Inc., New York, NY. Feb. 7, 2013.
Advertising Brochure: "XCL System", 2 pages, Innovation Sports of Foothill Ranch, CA. Feb. 7, 2013.
Advertising Brochure: "The 9 Innovations of the Axiom Custom Brace", 1 page, Bledsoe, Medical Technology, Inc. (2005).
Technical Manual: Bellacure: Restore Your Lifestyle, 10 pages, Bellacure, Inc. (2005).
Technical Manual: "Boa Technology", 3 pages, Boa Technology, Inc. of Steamboat Springs, CO, Feb. 7, 2013.
Advertising Brochure: "GII Unloader Select", 2 pagse, Ossur HF of Reykjavik, Iceland (visited Mar. 8, 2005), http://www.ossur.com/pring.asp?pageID=1729.
Advertisement: "McDavid Knee Guard and 155 Ligament Augmentation System", 3 pages, Advanced Brace of Irving TX (visited Mar. 8, 2005), http://www.supports4u.com/mcdavid/kneeguard.htm.
Advertisement: "Triax", 1 page, Lanxess AG (visited Mar. 8, 2005), http://www.techcenter.lanxess.com/sty/emea/en/products/description/57/index/jsp?print=true&pid=57.
Reference: "Anatomical Planes", 1 page, (visited Mar. 26, 2005), http://www.spineuniverse.com/displayarticle.phpo/article1023.html.
Advertisement: "M2 Inc. Parts Catalog", 3 pages, M2 Inc. of Winooski, VT (visited Mar. 29, 2005), http://www.m2intl.com/medical.MedClsr.htm.
Advertisement: "Axiom", 3 pages, Bledsoe by Medical Technology, Inc. (visited Jun. 15, 2005), http://www.bledsoebrace.com/custom/axiom.asp.
Advertisement: "Bellacure: The Treatment Device", 6 pages, Bellacure, Inc. (visited Jan. 5, 2006), http://www.bellacure.com/products/index/html.
Advertisement: "Lerman 3-Point Knee Orthosis", 2 pages, Becker Orthopedic of Troy, MI (visited Feb. 26, 2006), http://www.beckerortho.com/knee/3-point/htm.
International Search Report and Written Opinion from International Application No. PCT/US08/03237, Jul. 14, 2008, 10 pages.
Article: "Thermoplastic Elastomers TPE, TPR, TPV", 6 pages (visited Mar. 14, 2007), http://www.bpf.co.uk.bpfindustry/plastics_thermplasrubber_TBR.cfm.
European Search Report Issued in EP 10 17 2396, dated Oct. 25, 2010, 5 pages.
European Search Report Issued in EP 08 74 2047, dated Aug. 1, 2013, 6 pages.
International Search Report and Written Opinion from International Application No. PCT/IB2010/003540, dated Oct. 13, 2011, 6 pages.
International Search Report and Written Opinion International Application No. PCT/US2014/010410, dated May 2, 2014.
International Search Report and Written Opinion of the International Searching Authority from International Application No. PCT/US2014/014192, dated May 20, 2014.
International Search Report and Written Opinion from International Application No. PCT/US2013/069558, dated Jul. 3, 2014.
International Search Report and Written Opinion from International Application No. PCT/US2014/010407, dated Jul. 10, 2014.
International Search Report and Written Opinion from International Application No. PCT/US2014/033266, dated Jul. 23, 2014.
"Velstick semi-rigid Fastener Furnished in Separate, Mating Components", Velcro Fasteners, Spaenaur, Sep. 2, 2009, 2009, 1 Page.

* cited by examiner

ORTHOPEDIC DEVICE AND METHOD FOR SECURING THE SAME

FIELD OF THE DISCLOSURE

The present disclosure relates to an orthopedic device, and more particularly to an orthopedic device that provides stability, protection, support, rehabilitation, and/or unloading to a portion of the human anatomy in a streamlined and light manner.

BACKGROUND

Known orthopedic devices are used for providing stability, protection, support, rehabilitation and/or unloading a portion of the human anatomy. Known devices, however, are often considered as being physically bulky, heavy, and costly requiring numerous manufacturing processes to be produced.

An example of an orthopedic device is a knee brace. As is well understood, knee braces are widely used to treat a variety of knee infirmities. Such braces may be configured to impart forces or leverage on the limbs surrounding the knee joint to relieve compressive forces within a portion of the knee joint, or to reduce the load on that portion of the knee. If knee ligaments are weak and infirm, a knee brace may stabilize, protect, support, unload, and/or rehabilitate the knee.

The knee is acknowledged as one of the weakest joints in the body and serves as the articulating joint between the thigh and calf muscle groups. The knee is held together primarily by small but powerful ligaments. Knee instability arising out of cartilage damage, ligament strain, and other causes is relatively commonplace since the knee joint is subjected to significant loads during the course of almost any kind of physical activity requiring legs.

A healthy knee has an even distribution of pressure in both its medial and lateral compartments. It is normal for a person with a healthy knee to place a varus moment on the knee when standing so pressure between the medial and lateral compartments is uneven but still natural.

Compartmental osteoarthritis is a problematic type of knee infirmity. It may arise when there is a persistent uneven distribution of pressure in one of the medial and lateral compartments of the knee.

Compartmental osteoarthritis can be caused by injury, obesity, misalignment of the knee, or due to aging of the knee. A major problem resulting from osteoarthritis is that smooth cartilage lining the inside of the knee wears away. This leads to a narrowing of the joint space due to the development of cysts and erosions in the bone ends. Because of the narrowing of the joint, bone comes directly in contact with bone, and an uneven distribution of pressure develops across the knee, which may cause the formation of bone spurs around the joint. All of these changes ultimately lead to increasing pain and stiffness of the joint.

While there are no cures to osteoarthritis, there are many treatments. Individuals who have a diagnosis of isolated lateral or medial compartmental osteoarthritis of the knee are confronted with a variety of treatment options such as medications, surgery, and nonsurgical interventions. Nonsurgical interventions include using canes, lateral shoe wedges, and knee braces.

Knee bracing is useful in providing compartment pain relief by reducing the load on the compartment through applying an opposing external valgus or varus moment about the knee joint. Unloading knee braces have been shown to significantly reduce osteoarthritis knee pain while improving knee function.

While known knee braces succeed at reducing pain or at stabilizing a knee joint, many users find these braces to be bulky, difficult to don, complicated to configure, and uncomfortable to wear. The exemplary embodiments described have streamlined features capable of providing relief for medial or lateral compartmental osteoarthritis, or functional stability of the knee without the attendant drawbacks of known unloading knee braces.

The concepts described with the exemplary knee brace embodiments may be extended to a variety of wearable devices configured to be secured to and/or support numerous portions of anatomy.

SUMMARY

The embodiments of the orthopedic device are described in the context of a knee brace for providing relief to users with complications of the knee, such as with osteoarthritis. The embodiments offer a knee brace having a low profile and simpler to use than conventional braces aimed at treating osteoarthritis of the knee. The knee brace embodiments define a sleeve-like configuration concealing and confining certain brace components such as straps and portions of the frame. In this manner, the hidden mechanics provide a discreet appearance with easy access, with or without the zipper described below, for initial fit requirements and adjustment.

The embodiments offer a lighter and more versatile knee brace, and may include a soft inner sleeve segment that makes the brace easier to don and doff. A single adjustment mechanism allows for a plurality of straps to be simultaneously adjusted without the necessity for adjustment of other straps. Zipper configurations assist the user to don and doff the brace, especially those with irregular or disproportionate body types and/or with poor hand dexterity in their hands. The combination of a sleeve and zipper simplifies the donning and doffing process, particularly in view of the user being able to slide the brace on in its entirety. The zipper allows access to various components of the brace ordinarily concealed during normal use of the brace. The components of the brace are trimmable and adjustable to allow for use across a spectrum of user profiles and anatomies.

In an embodiment, the orthopedic device includes an inner sleeve segment having interior and exterior surfaces, a frame applied over the outer surface of the inner sleeve, at least one strap connected to the frame, and an outer sleeve segment connected to the inner sleeve segment and having interior and exterior surfaces with the interior surface facing the interior surface of the inner sleeve segment. A portion of the frame may be confined within a space defined between the outer and inner sleeve segments forming a definitive sleeve.

The outer sleeve segment may extend over only a portion of the inner sleeve to define a pocket into which a portion of the frame extends, such as a frame shell. The pocket may include openings to permit elements of the knee brace to extend outwardly from the shell within the pocket, and such elements may include a strap, strut, hinge or other brace component. The outer sleeve segment may include reinforcement edging about the openings and/or the periphery of the outer sleeve segment to improve durability of the periphery of the outer sleeve segment and improve the ornamental appearance of the device.

The inner and outer sleeve segments are preferably formed from latex-free fabrics. The interior surface of the inner sleeve segment is soft and comfortable to the touch and provides a barrier from the frame for skin-sensitive users. The inner sleeve segment may include padding incorporated therewith and associated with the frame to eliminate a necessity for additional padding that may attribute to increased weight.

In a variation, the orthopedic device may include multiple outer sleeve segments for concealing or covering various components over certain lengths over the inner sleeve segment.

The inner sleeve segment may extend the entire length of the orthopedic device, only over a portion of the length of the orthopedic device, or may have multiple segments defining various sections of an inner periphery of the orthopedic device.

In a variation, the outer sleeve segment may extend the entirety of the length of the inner sleeve segment, and the combination of the inner and outer sleeve segments may define an entirety of the length of the orthopedic device.

The frame is selectively accessible from the outer surface of the outer sleeve in that a user or clinician can withdraw portions of the frame from the sleeve for adjustments. From this arrangement, the orthopedic device is easily modifiable and can be adjusted during the treatment of a user, including changing the length of the at least one strap and customizing the frame to suit the anatomy of a user.

The orthopedic device may include a tensioning mechanism coupling a first end of the at least one strap to the frame. The tensioning mechanism provides incremental adjustment of the first end of the at least one strap relative to the frame among a plurality of predetermined settings. The tensioning mechanism may be mounted to an outer surface of the frame and is preferably accessible from and through the exterior surface of the outer sleeve segment.

The tensioning mechanism may include a rotary ratchet and a winding mechanism. The first end of the at least one strap may be coupled to the tensioning mechanism by a cable windable about the winding mechanism; the rotary ratchet keeps the winding mechanism from releasing unless the winding mechanism is selectively released by the user. The tensioning mechanism allows for simple and repeatable dosing of pain-relieving forces, particularly simplifying the adjustment process so two straps can be finely tensioned simultaneously.

The frame may define upper and lower shells, with a hinge that connects and spaces them apart. The upper and lower shells may be rigid or semi-rigid, or alternatively may be flexible but become semi-rigid when the at least one strap is tensioned and the orthopedic device is placed snugly over the leg of the user. When semi-rigid, the shells may accommodate movement of the leg of the user, but also firmly secure to the leg and reinforce the leg. The shells are of a low profile type, thereby reducing the weight of the knee brace.

The frame preferably defines a "single upright frame" in that struts connect the upper and lower shells to one another along a single side of the brace. The knee brace is considered lightweight in that it preferably has a weight in the range of 200-500 grams. The struts may be thinner over conventional struts, particularly since they combine with the sleeve to secure over the leg of the user. The struts are connected to one another by a hinge.

The at least one strap may be adjustable in length within the space between the outer and inner sleeve segments. The at least one strap may have first and second ends connecting to and spiraling between the upper and lower shells. The first and second ends may connect at a first side of the upper and lower shells, and extend over a second side of the brace located opposite to the first side at which the hinge is located.

In a variation, the at least one strap has first and second ends connected to the frame, the first end of the least one strap is adjustably movable relative to the frame and the second end of the at least one strap is anchored to the frame. The orthopedic device may further comprise a bracket connected to and extending from the at least one strap. The tensioning mechanism may be connected to the frame and couple the first end of the at least one strap to the frame by the bracket. The tensioning mechanism may be arranged to simultaneously adjust the at least one strap relative to the frame. The tensioning mechanism includes a winding mechanism, and at least one cable extends from the winding mechanism and couples to the bracket.

The bracket may define a channel through which first and second portions of the at least one cable extend. The first cable portion secures to the frame at an anchor point, and the second cable portion operatively engages the tensioning mechanism to allow for selective reduction in length of the second cable portion for adjusting the at least one strap relative to the frame. The channel permits more uniform pulling or movement of the at least one strap by the cable by distributing the tension of pulling more uniformly across the width of the at least one strap.

Alternatively or in combination with the channel, the bracket may define an opening through which the cable may also extend and pull the bracket and strap from a single point at the bracket. In this manner, a pull angle of the at least one cable may adjust according to the angle the strap is at any point in adjustment of the at least one strap.

In an embodiment, the at least one strap defines first and second straps. The at least one cable operatively engages first and second brackets extending respectively from said first and second straps. The tensioning mechanism is arranged to operatively wind the at least one cable so the first and second straps are adjusted simultaneously.

A guide may be on the frame and extend between the bracket and the winding mechanism. The guide routes the second cable portion to the winding mechanism. In a variation, the guide may be pivotally secured to the frame and pivot according to the angle at which the at least one strap is arranged relative to the axis or axes of the first and second struts. The guide may be also initially adjusted at an angle and secured and maintained at the angle.

The orthopedic device may also have a strap tab bearing tightening indicia and at the first end of the at least one strap. The strap tab is arranged for substantial adjustment of a length of the at least one strap, and the tensioning mechanism is arranged for finer adjustment of the at least one strap relative to the frame.

At least one of the upper and lower shells may define a flexible edge portion located along a periphery. The upper and lower shells may each be formed from a main body, and the flexible edge portion may also be formed from the main body. The flexible edge portion may only be formed along a side of the upper and lower shells opposite to a side adjacent the hinge.

A first zipper may be on the outer sleeve and secured to opposed edges of the outer sleeve to separate the opposed edges and provide access to the frame and the at least one strap. The first zipper may be at the lower portion of a first side of the orthopedic device, and the at least one strap may be connected to the frame at the first side of the orthopedic device.

The outer sleeve segment may be defined by at least first and second material sections. The first material section may generally correspond in shape to the frame, and the second material section may be secured to the first material section such that the second material section covers portions of the at least one strap extending past the frame. The first material section may have padding and breathability features different from the second material section.

The numerous advantages, features, and functions of embodiments of the orthopedic device will become readily apparent and better understood in view of the following description and accompanying drawings. The following description is not intended to limit the scope of orthopedic device, but instead merely provides exemplary embodiments for ease of understanding.

The drawing figures are not necessarily drawn to scale, but instead are drawn to provide a better understanding of the components, and are not intended to be limiting in scope, but rather to provide exemplary illustrations. The figures illustrate exemplary configurations of an orthopedic device, and in no way limit the structures or configurations of an orthopedic device and components according to the present disclosure.

DETAILED DESCRIPTION OF VARIOUS EMBODIMENTS

A. Environment and Context

An embodiment of an orthopedic device in the form of a knee brace is provided to reduce the effect of osteoarthritis in a knee joint and/or stabilize a knee joint weakened by injury or other infirmities. Although the illustrated embodiments show a hinge positioned on the medial side of the knee brace and the straps positioned on the lateral side of the knee brace, it will be understood that the knee brace may be configured to reduce or cure both medial and lateral knee joint infirmities. The hinge may be positioned on the lateral side of the knee brace and the straps may be positioned on the medial side of the knee brace.

The knee brace embodiments of the disclosure are adapted for a human knee joint, and may be dimensioned to accommodate different types, shapes, and sizes of human joints, appendages, and other anatomical portions. Embodiments may be provided to orient principal forces exerted by strap systems of the embodiments at any desirable location to treat knee infirmities.

For explanatory purposes, the knee brace embodiments are described and divided into sections denoted by general anatomical terms for the human body. Each of these terms is used in reference to a human leg divided in similar sections with a proximal-distal plane extending along the meniscus of the knee between the femur and tibia (i.e., femoral and tibial leg portions, respectively).

The embodiments of the knee brace are also divided into anterior and posterior sections by an anterior-posterior plane. The anterior-posterior plane generally corresponds to the coronal or frontal plane of a human leg. Each of the anterior and posterior sections is further divided about the center of the knee by a transverse or proximal-distal plane and median, sagittal, or lateral-medial planes.

The anatomical terms described are not intended to detract from the normal understanding of such terms as readily understood by one of ordinary skill in the art of orthotics. It will also be understood that, while the invention is discussed with a knee brace, the principles described can be extended to a variety of orthopedic and prosthetic devices, and any other device that would be wearable and employ the features described.

B. Embodiments of the Orthopedic Device

Figure 1:
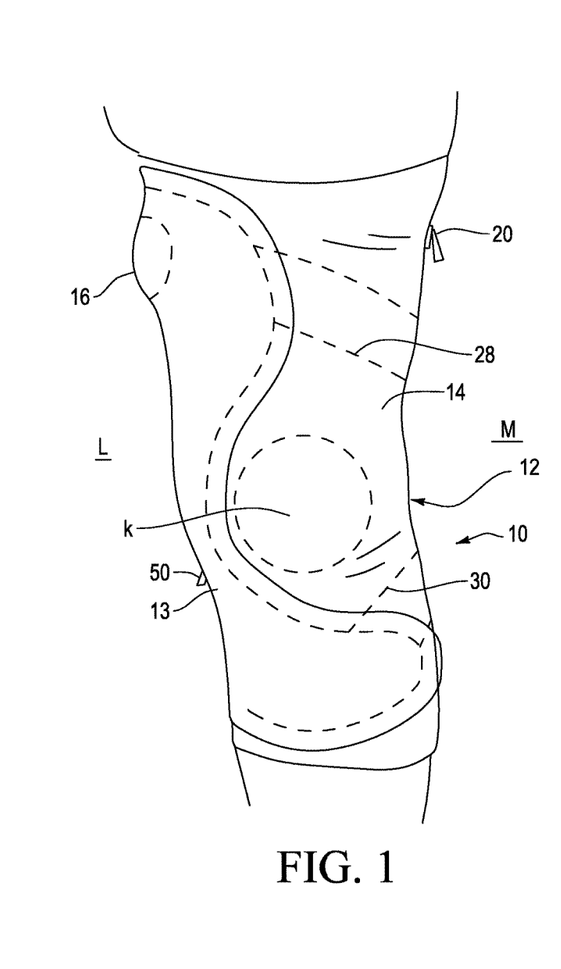
FIG. 1 is a front elevational view according to an outer configuration of an embodiment of the orthopedic device.

FIG. 1 shows an outer configuration of an orthopedic device 10 in the form of a knee brace for securing about a knee K. The device 10 has an outer sleeve 12 covering various brace components, as disclosed in FIG. 2, and including a plurality of straps 28, 30 extending about lateral L and medial M sides of the device and underneath the outer sleeve 12. A tensioning mechanism 18 protrudes from a first side, such as lateral side L, of the device 10.

Figure 2:
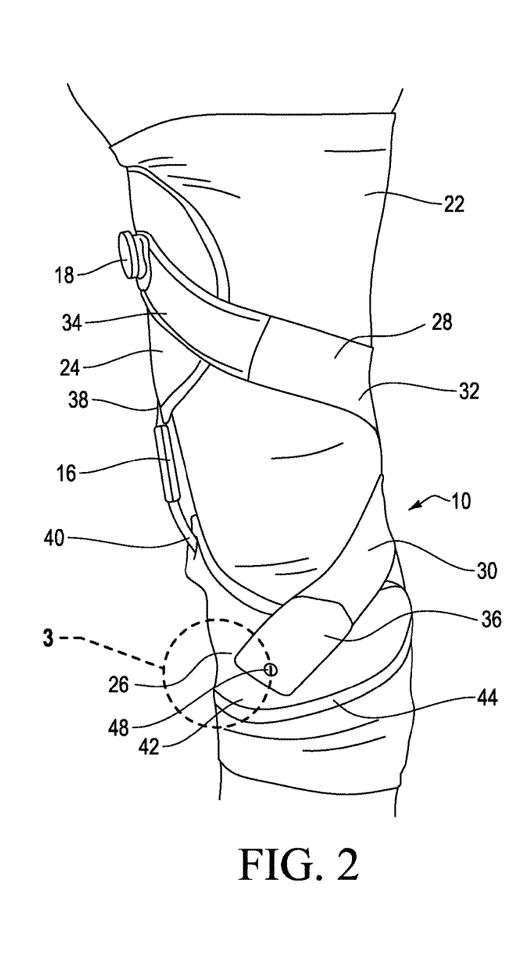
FIG. 2 is a front elevational view according to an inner configuration of the embodiment of FIG. 1.

FIG. 2 shows an inner configuration of the knee brace 10. The brace 10 includes an inner sleeve segment 22 having inner and outer surfaces, a frame comprising upper and lower shells 24, 26, respectively connected to and spaced apart by upper and lower struts 38, 40, respectively, secured to a hinge 16, and the first and second straps 28, 30 connecting to the upper and lower shells 24, 26. The frame, straps, and hinge with the struts are preferably confined within a space defined between the inner and outer sleeves 12, 22, and concealed along both interior and exterior peripheral surfaces of the device 10.

The shells 24, 26 include padding 44 extending along the inner surface of the shells and located adjacent to an outer surface of the inner sleeve segment 22. The padding 44 is sandwiched between the shells 24, 26 and the inner sleeve segment 22. The padding 44 preferably extends beyond the peripheral edges of the shells and along the entirety of the inner surface of the shells.

Figure 3:
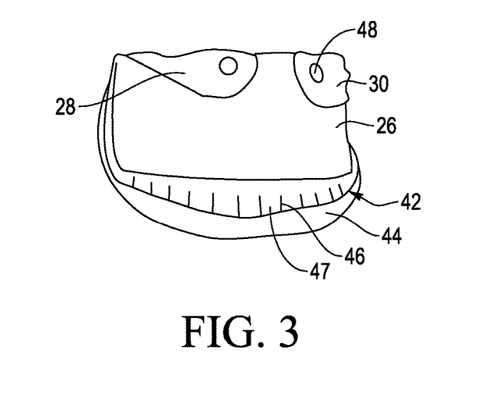
FIG. 3 is a detail view of detail III in FIG. 2 showing a flexible edge portion.

As shown in detail III depicted in FIG. 3, at least one of the upper and lower shells 24, 26 defines a flexible edge portion located along a periphery. The lower shell 26 defines the flexible edge portion 42 at a lowermost edge opposite the upper most edge adjacent to the hinge 16. The flexible edge portion 42, in this variation, is formed by a plurality of gaps 46 extending a distance into the lower shell from the periphery of the lower shell 26. A plurality of individually flexible sections 47 is formed between each of the gaps 46 to form the flexible edge portion 42.

According to this variation, the lower shell is formed from a main body, and the flexible sections 47 are formed from the main body itself (as opposed to being a structural element apart or separate from the main body). Alternatively, the flexible edge portion may be formed from an overmold having softer properties than the main body, as taught in U.S. Pat. No. 7,198,610, granted Apr. 3, 2007, and incorporated herein by reference.

The flexible edge portion 42 may be only formed along a side of the upper and lower shells opposite to a side adjacent the hinge 16, or may be arranged at any other location along the shells 24, 26. The flexible edge portion 42, at least in the embodiment of FIG. 3, extends short of the padding 44, and beyond the peripheral edge of the shell 26.

Each of the shells may be formed from a flexible, thin, and soft plastic enabling trimming of the dimensions of each of the shells.

Referring to FIG. 2, each of the first and second straps 28, 30 has first and second ends connecting to and spiraling between the upper and lower shells 24, 26. The first and second ends of the straps connect at the first side, such as the lateral side L, of the upper and lower shells. The straps 28, 30 also extend over to the second side, such as the medial side M, of the brace located opposite to the first side at which the hinge 16 is located. The orientation of the brace can be reversed so that the straps are arranged in an opposite orientation.

The straps are arranged in an orientation so as to treat osteoarthritis, as principally taught in U.S. Pat. No. 7,198,610. The brace is not limited to two straps and may only include a single strap connecting the upper and lower shells, as likewise taught in U.S. Pat. No. 7,198,610.

Each of the straps 28, 30 is adjustable in length and tensionable within the space between the outer and inner sleeve segments 12, 22.

According to the embodiment of FIG. 2, the straps 28, 30 may each include an elastic segment 34 at a first end and connecting to the upper shell 24, and a non-elastic segment 32 extending from the elastic segment 34. The non-elastic segment 32 preferably forms a majority of the length of the straps. Each of the straps may include an anchor segment 36 at a second end of the straps and is pivotally attached to the lower shell 26. The anchor segment 36 is preferably more rigid than the non-elastic segment 32. The elastic segment allows for gentle adjustment of the strap over the user's leg, whereas the non-elastic segment is provided to resist movement of the knee to sufficiently unload a compartment of the knee.

The anchor segment 36 may form a segment of the length of the straps, or may alternatively be formed as a reinforcement part which extends over at least a portion of the second end of the non-elastic segment 32. Preferably, the anchor segment 36 pivotally connects at an anchoring pivot point 48 to the lower shell to provide adjustability of the second of the strap relative to the lower shell. The anchor segment may be more rigid than the non-elastic segment, and may be formed by a flexible plastic piece whereas the non-elastic segment may be formed from a textile. Examples of the non-elastic segment may be found in U.S. Pat. No. 7,198,610 by way of the force and stability straps discussed in the patent.

The second end of the straps is preferably trimmable in length. According to an embodiment, the anchor segment 36 is removably attached to the non-elastic segment 32 via a hook and look attachment. The second end of the non-elastic segment 32 can be removed from the anchor segment 36, trimmed in length, and then reattached to the anchor segment 36.

Figure 4:
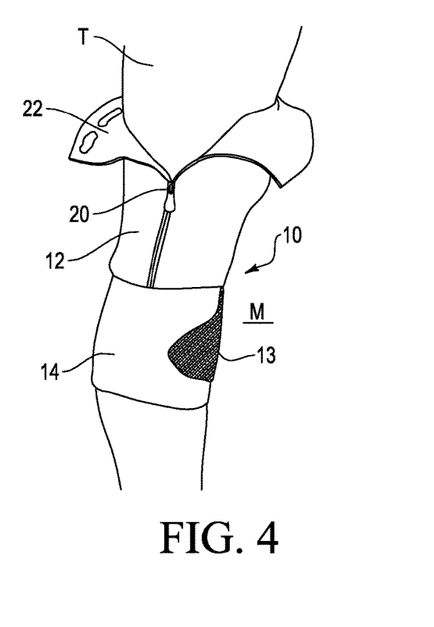
FIG. 4 is a schematic view showing a medial side of the orthopedic device of FIG. 1 in an open thigh mode.

As shown in FIG. 4, the brace 10 includes an upper zipper 20 secured to the outer and inner sleeve segments 12, 22 and arranged to separate opposed edges of the outer and inner sleeve segments at a second or medial side M of an upper portion of the knee brace. The brace 10 is therefore operable at its upper portion corresponding to the user's thigh, and assists the user when the brace is donned and doffed. The user can unzip the upper portion of the brace when donning the brace to accommodate the thigh and facilitate correct placement of the brace over the user's knee. Because the outer and inner sleeve segments 12, 22 have some flexibility, the brace can be tightly secured over the thigh T after the upper zipper 20 is zipped.

Figure 5:
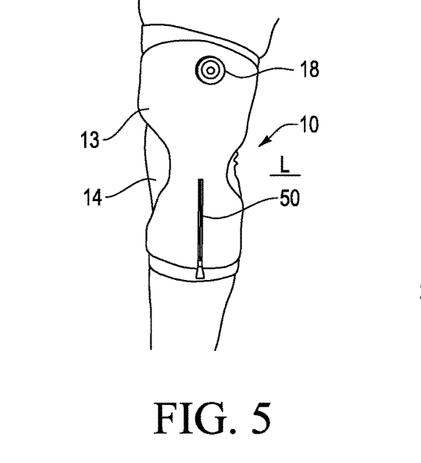
FIG. 5 is a schematic view showing a lateral side of the orthopedic device of FIG. 1 in a closed calf mode.
Figure 6:
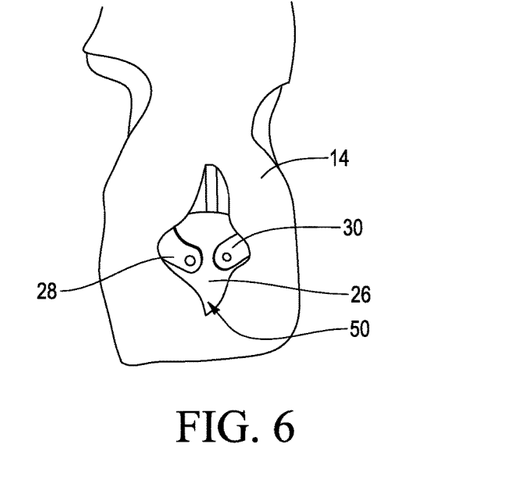
FIG. 6 is a schematic view showing the lateral side of FIG. 5 in an open calf mode.

FIG. 5 shows a lower zipper 50 in a closed configuration and provided on the outer sleeve 12 to secure opposed edges of the outer sleeve or separate the opposed edges to provide access to the frame and the straps, as shown in FIG. 6. The lower zipper 50 is on the first or lateral side L of the brace to allow for better access of the brace components for resizing and adjustment. In this embodiment, the lower zipper 50 is preferably only on the outer sleeve and may only travel within a section of the lower portion of the outer sleeve and may be spaced away from the lower peripheral edge of the outer sleeve, as depicted in FIG. 6.

In a variation, the lower zipper 50 may extend along any segment or length of the outer sleeve segment. It may extend between the uppermost and lowermost peripheral edges of the outer sleeve. Other variants are envisioned in that the lower zipper may not be confined within the length (corresponding to longitudinal length of the leg), and may split open the outer sleeve much in a manner shown and described with the upper zipper.

Multiple zipper configurations may be arranged in that a first zipper segment extends from the uppermost periphery of the outer sleeve to a hinge region generally corresponding to the hinge, and another zipper extends from the lowermost periphery of the outer sleeve to the hinge region. The zipper or zippers on the outer sleeve may be provided along any side of the brace and is/are not limited to only the lateral side.

The outer sleeve 12 may define first and second material sections 13, 14. The first material section 13 generally corresponds in shape to a frame of the brace, and the second material section 14 is secured to the first material section. The second material section 14 covers portions of the straps 30, 32 extending past the frame.

The first material section has padding and breathability features different from the second material section. The first material section may be formed from a spacer material comprising a three-dimensional knit structure covered by a mesh that provides sufficient breathability, insulation, compression, durability, and recovery. An exemplary material is produced by Gehring Textiles under product numbers SHR 701, SHR 714 or SHR 754F.

The second material section and the inner sleeve segment may be constructed of the same or different fabrics. Exemplary fabrics include spandex, Lycra, nylon, polyester, OUTLAST, COOLMAX, AEROSPACER, microfiber, three-dimensional fabrics, and other suitable fabrics. The sleeve is preferably constructed from a latex-free fabric that provides a fabric-lined inner surface preferably providing a soft and comfortable feel and a barrier from the brace for skin-sensitive users.

The sleeve may have various treatments incorporated therein including antibacterial, scenting, and moisture wicking agents. Frictional features may be at various locations along the inner surface of the inner sleeve segment. Silicone bands, dots, segments or other configurations may be at the uppermost section of the upper portion of the inner sleeve segment to prevent slippage of the brace on the thigh of the user. Alternatively, frictional features may be provided along the inner surface of the inner sleeve segment corresponding to the shells.

The inner and outer sleeves may have elasticity to allow for the brace to be tightly and comfortably secured over the leg, particularly by application of the upper zipper. The elasticity of the inner and outer sleeves may remove necessity for circumferential straps provided besides the aforementioned straps 28, 30.

Figure 7:
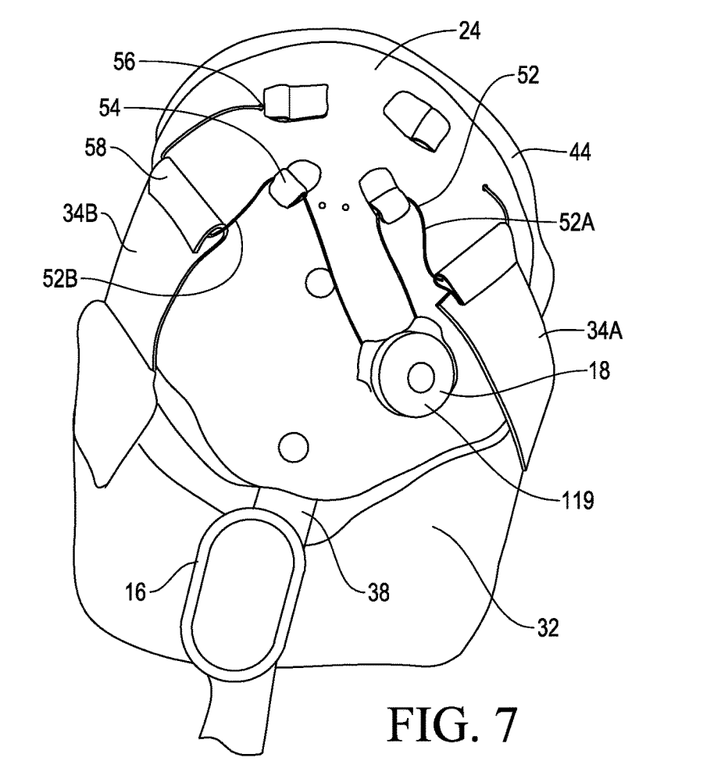
FIG. 7 is a detailed view of the outer surface of the upper shell and tensioning mechanism of FIG. 2.
Figure 8:
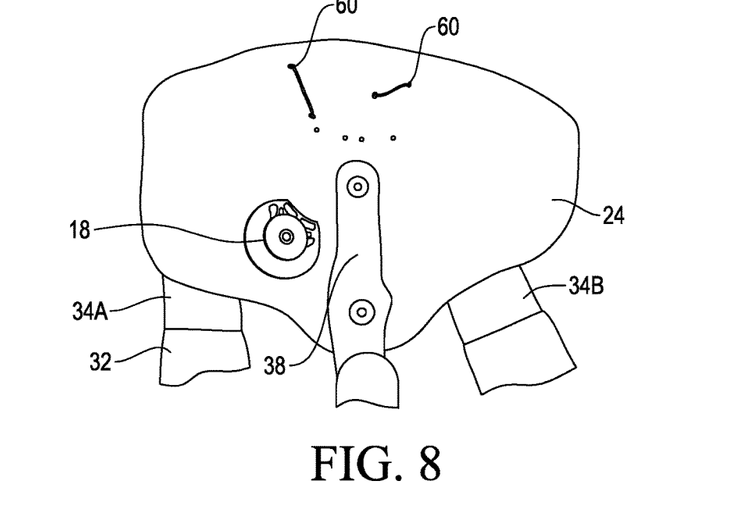
FIG. 8 is a detailed view of the inner surface of the upper shell and tensioning mechanism of FIG. 2.

Referring to FIGS. 7 and 8, the tensioning mechanism 18 couples a first end of the straps 28, 30 to the frame. The tensioning mechanism 18 provides incremental adjustment of the first end of the straps relative to the frame among a plurality of predetermined settings. The tensioning mechanism may be a dial tensioning device, a ladder strap or other suitable incremental tensioning mechanism, as taught in U.S. Pat. No. 7,198,610.

The tensioning mechanism may include a rotary ratchet and winding mechanism. The first ends of the straps are each coupled to the tensioning mechanism 18 via a cable 52 having a first end windable about the tensioning mechanism 18 and a second end 60 anchored to the upper shell. The cable 52 has segments 52A, 52B extending from the tensioning mechanism 18 routed through cable guides 54 to a bracket 58 mounted on the elastic segments 34A, 34B and placed through openings 56 formed by the upper shell 24 to anchor to the shell. A knob 119 is operatively connected to the rotary ratchet and the winding mechanism may protrude outwardly from the knee brace and outside the sleeve.

From the arrangement in FIGS. 7 and 8, the first and second straps are each coupled to and simultaneously adjustable by the tensioning mechanism, permitting the straps to be adjusted with a single mechanism. The elastic segment allows for some ease in the strap to compensate for the inelasticity of the non-elastic segment preferably provided to apply a greater amount of pressure against the knee as the tensioning mechanism is used to apply tension in the straps over the user's leg. The combination of the elastic and non-elastic segments in combination with the tensioning mechanism provides a balance in maintaining sufficient tension in the strap to make the straps more comfortable to the user.

Figure 9:
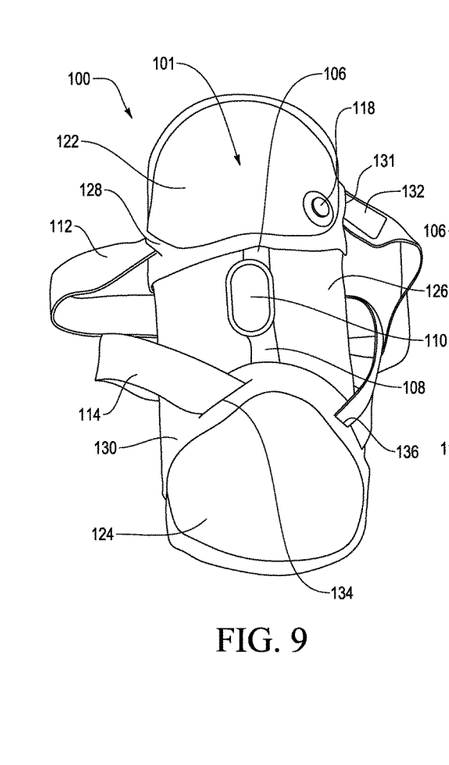
FIG. 9 is a front elevational view of another embodiment of the orthopedic device having a sleeve.
Figure 10:
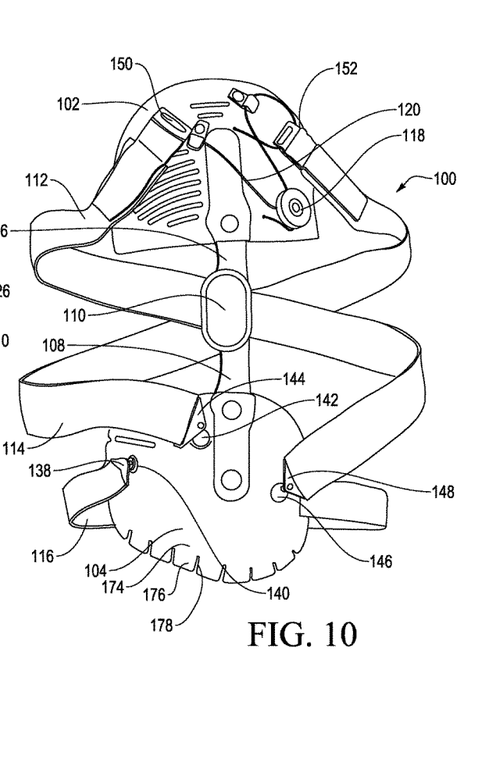
FIG. 10 is a front elevational view of the embodiment of FIG. 9 without the sleeve.

Referring to the orthopedic device 100 of FIGS. 9 and 10, the device 100 includes upper and lower shells 102, 104, respectively connected to one another by a strut assembly including upper and lower struts 106, 108 connected to one another by a hinge 110. The longitudinal axis or axes (when the hinge is bent) of the brace may be considered to generally extend parallel to the upper and lower struts. First and second straps 112, 114 spiral between the upper and lower shells 102, 104. Either of the straps 112, 114 may be incrementally adjusted by a tensioning mechanism 118 connected to a cable 120 routed about one of the upper and lower shells.

Brackets or tab elements 150, 152 carried by first end portions of the straps 112, 114 are coupled to the cable 120 and permit adjustment relative to the upper and lower shells 102, 104. Second end portions of the straps 112, 114 may include fastener tabs 144, 148 coupling to openings 142, 146, such as those having a keyhole configuration with one end having a smaller diameter than another end of the opening. At least one end of the strap includes a strap tab 132 including tightening indicia.

A lower stability strap 116 may circumferentially extend about a lower portion of the device in combination with the lower shell 104. The stability strap 116 may have a first end carrying a fastener tab 138 engageable with an opening 140, and a second end looped about an opening defined by the lower shell 104.

The shells are of a low profile type and are preferably constructed from plastic, thereby reducing the weight of the knee brace. While the shells are preferably constructed from plastic, whether it is rigid, semi-rigid or flexible, the shells may be constructed from other known structural materials that are rigid, semi-rigid or flexible. The shells preferably have a thickness within the range of 1.0 mm to 5.0 mm and more particularly, within the range of 1.5 mm to 2.5 mm. The struts may be thinner over conventional struts particularly since they combine with the sleeve to secure over the leg of the user, and may be constructed from a plastic or metal. An aim of the device is to provide a lightweight orthopedic device, and the overall weight of the device is preferably within the range of 200 to 500 grams.

In this embodiment, the lower shell 104 defines a plurality of flexible edge tabs 176 spaced apart by gaps 178, and extend from the main body portion 174 and along the periphery of the lower shell 104. The flexible edge tabs are preferably oriented to generally descend downwardly toward the periphery of the lower shell, but can be oriented in a variety of directions to provide optimal pressure relief along the periphery of any shells used in the brace. The gaps may be uniformly spaced or alternative may be varied in width according to a desired degree of pressure relief sought in the brace.

It is preferable that the shell is thin so the flexible edge tabs 176 can flex over the leg of the user when the brace is worn and the flexible edge tabs can extend continuously from the main body portion without interruption. The flexible edge tabs may be formed when the lower shell is created by injection molding or other molding techniques using a polymer and forming the flexible edge tabs with the other portions of the lower shell in the same process step, preceding or subsequent process step. In this manner, the flexible edge tabs 176 provide greater comfort to the user over braces without flexible edges. The flexible edge tabs may have a thickness substantially the same as the remainder of the main body portion, or may taper in thickness as they extend to the periphery of the lower shell.

In a variation, the flexible edge tabs may be initially formed in a connected manner in that material extends between each of the tabs, without the gaps. For example, the tabs may be formed with thinned sections therebetween which enable a clinician to easily cut the thinned sections or selectively cut certain thinned sections to separate the tabs from one another and thereby form gaps.

As shown in FIG. 9, the device may include a sleeve 101 having upper and lower pockets 122, 124, respectively, adapted to hold the upper and lower shells 102, 104. The pockets 122, 124 are secured to a sleeve body 126. The pockets 122, 124 may be constructed by a thicker or more padded material than the sleeve body 126 which may be substantially flexible and breathable, and have characteristics of other sleeve embodiments discussed.

The pockets 122, 124 may include reinforcement edging 128, 130 about the pockets and may also include a surface of hook material for engaging opposing material of the pockets. In a preferred embodiment, the reinforcement edging may be less flexible and have greater toughness than material forming the outer sleeve segment. The pockets may include various openings 131, 134, 136 for permitting the straps and stability strap to extend about the exterior of the sleeve 101 and be secured to the shells.

Figure 11:
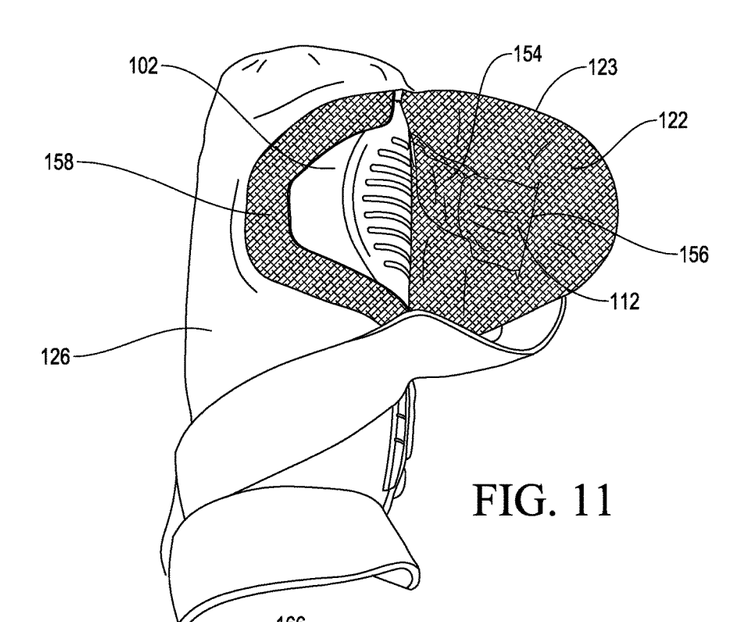
FIG. 11 is a schematic view of a pocket on the sleeve of the orthopedic device of FIG. 9.

FIG. 11 exemplifies the pocket 122 having an outer flap 123 arranged for opening and exposing at least part of the shell. The pocket 122 includes an inner rim 158 bearing fastener elements over a surface and engageable with a hook-receivable surface along the outer flap 123. Alternative fasteners may be used such as zippers, buttons, hooks, etc. The inner rim 158 is preferably flexible to permit entry of the shell into the pocket 122 and extends over at least a portion of the shell to retain the shell in the pocket. The pocket includes a cavity into which a portion of the shell extends beyond the outer flap.

The outer flap 123 may include an opening or slit 156 through which the strap 112 may extend when coupled to the shell. The strap 112 may be coupled to the shell via a coupling element, such as a clamping tab 154 with hook elements engageable with a hook-receivable surface on the straps, to a bracket or tab coupled to the cable.

Figure 12:
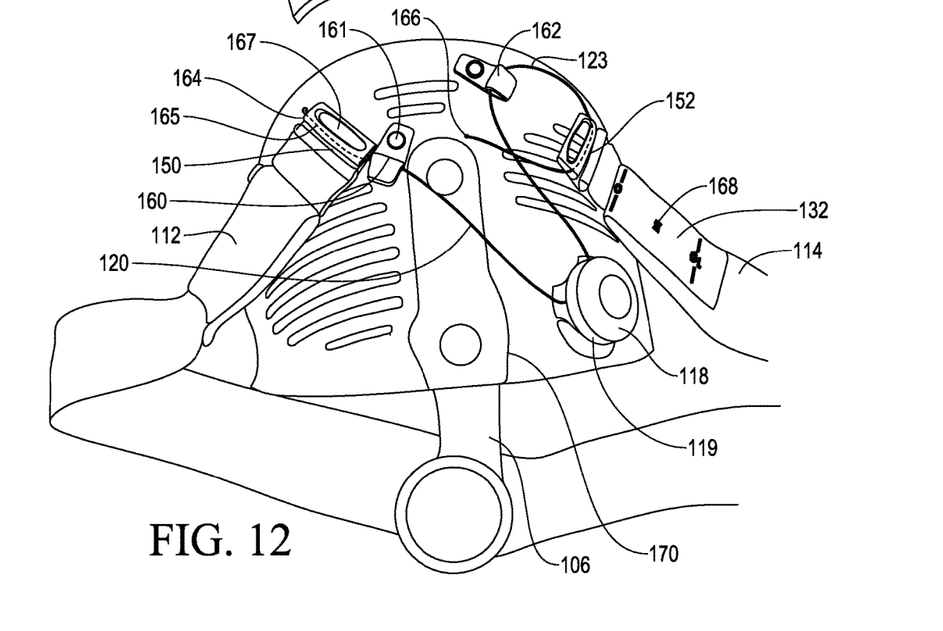
FIG. 12 is a detailed view of the inner surface of an upper shell in the orthopedic device of FIG. 9.

Referring to FIG. 12, a tightening system may include the tensioning mechanism 118 for adjusting the cable 120 by rotary motion. In this embodiment, as with the embodiment of FIG. 7, both of the straps 112, 114 are preferably singularly adjusted by the tensioning mechanism 118. The ends of the cable 120 at a first portion (not shown) are anchored at points 164, 166 corresponding respectively to the straps 112, 114.

Each of the straps includes the brackets 150, 152 through which the cable 120 extends from the anchor points 164, 166, and the cable has a second portion 123 which thereafter the cable is routed by guides 160, 162 toward the tensioning mechanism in an appropriate manner, such as the manner depicted in FIG. 12. The guides 160, 162 may either be secured in orientation against the frame, or pivotally secured by pivot pin 161.

The brackets 150, 152 may each include a channel 165 through which the cable 120 extends transversely relative to the strap length to distribute tension across the width of the strap when the strap is tensioned. The clamping tabs 132, secure to the straps and extend from the brackets to permit sizing of the length of the straps. The brackets 150, 152 may also define a central opening 167 at an end portion located opposite the end secured to the straps. The central opening 167 provides means through which the cable may pass and slide according to the orientation of the strap relative to an axis of the brace.

The shells may be configured to receive an end portion of the struts, such that strut 106 is received in a cavity 170 formed by the shell. In this manner, the strut and inner surface of the shell define a continuous surface without protruding relative to one another along the interior of the shell and are intended to be adjacent to the leg of the user. In a variation, an indent may be provided in the shell only equal to half of the strut thickness, and the strut is not flush with the shells.

Figure 13:
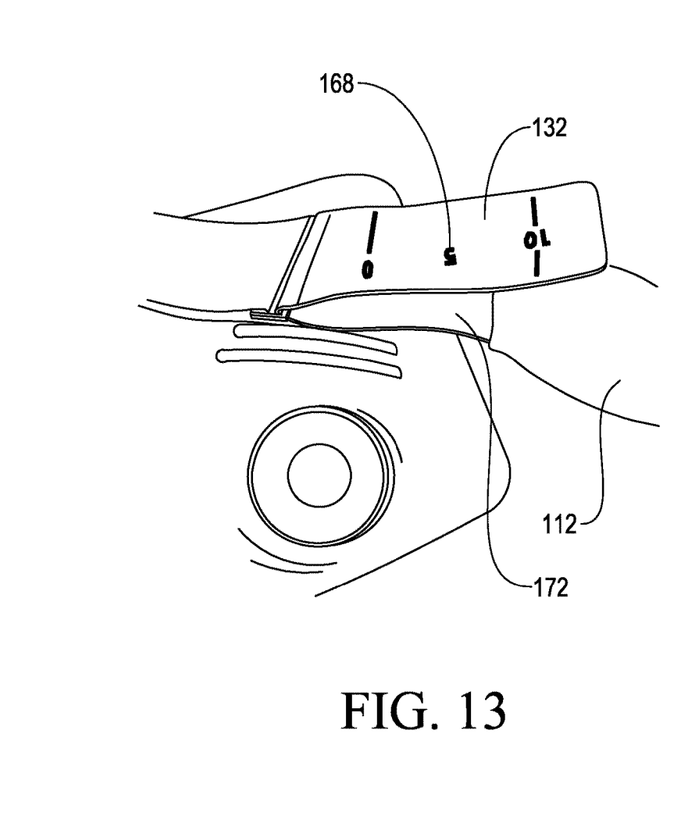
FIG. 13 is a detailed view showing a strap tab including tightening indicia.

FIGS. 12 and 13 show the strap tab 132 as a clamping tab bearing indicia 168 the user may employ to understand relative settings of the strap 112. The clamping tab 132 includes hook material 172 on both flaps clamped onto an end of the strap 112. The border of the sleeve at the slit may serve as an indicator at which the indicia falls when the strap 112 is adjusted.

Figure 14:
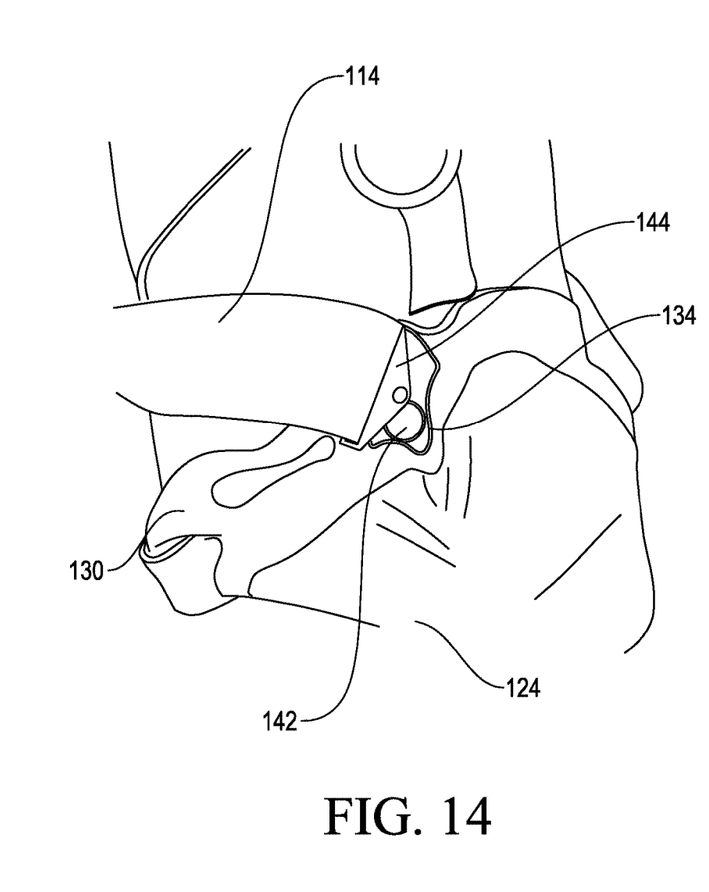
FIG. 14 is a detailed view showing attachment of a strap onto a lower shell in the orthopedic device of FIG. 9.

FIG. 14 exemplifies how the strap 114 may couple to the lower shell 104 when the lower shell 104 is placed into the pocket 124. The strap 114 carrying the fastener tabs 144 secures to the opening 142. The strap 114 extends through the slit or opening 134 defined by the pocket 124 and is preferably formed about the reinforcement edging 130 located about the periphery of the pocket 124.

Various methods for donning and doffing the brace may be permitted in combination with the various features and components discussed in view of the embodiments of the knee brace. A method for donning the brace may include unzipping the upper zipper prior to placing the brace over the user's leg to open at least the thigh section, and then subsequently zipping the upper zipper once the knee brace is properly on the user's leg to close the brace. The lower zipper may be unzipped to provide access to the shells and straps to allow for trimming of the shells and straps. The straps may be adjusted simultaneously to tension the straps over the user's leg.

Of course, it is to be understood that not necessarily all objects or advantages may be achieved in accordance with any particular embodiment of the disclosure. Thus, for example, those skilled in the art will recognize that the orthopedic device may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct an orthopedic device in accordance with principles of the present disclosure. Additionally, it will be understood by the skilled artisan that the features described herein may be adapted to other types of orthopedic devices. Hence this disclosure and the embodiments and variations thereof are not limited to knee braces, but can be utilized in any orthopedic devices.

Although this disclosure describes certain exemplary embodiments and examples of an orthopedic device, it therefore will be understood by those skilled in the art that the present disclosure extends beyond the specifically disclosed knee brace embodiments to other alternative embodiments and/or uses of the disclosure and obvious modifications and equivalents thereof. Thus, it is intended that the scope of the present disclosure should not be limited by the particular disclosed embodiments described above, and may be extended to orthopedic devices and supports, and other applications that may employ the features described herein.

The invention claimed is:

1. An orthopedic device, comprising:
a frame including a first shell;
a first strap having a first end connected to the first shell by a cable;
a tensioning mechanism connected to the cable and arranged to provide incremental adjustment of the cable among a plurality of predetermined settings;
at least one guide secured onto the first shell, the cable extending through the at least one guide between the tensioning mechanism and the first strap;
wherein the tensioning mechanism includes a rotary ratchet and a winding mechanism;
wherein the first strap includes a non-elastic segment and an elastic segment at the first end thereof carrying a bracket coupling to the cable.

2. The orthopedic device of claim 1, wherein the tensioning mechanism is mounted directly onto the first shell.

3. The orthopedic device of claim 1, wherein the tensioning mechanism includes a knob operatively connected to the rotary ratchet and the winding mechanism, the orthopedic device further comprising a sleeve extending over the first shell and the knob protruding outwardly from the orthopedic device and outside the sleeve.

4. The orthopedic device of claim 1, wherein the cable has a first end windable about the tensioning mechanism and a second end anchored to the first shell.

5. The orthopedic device of claim 1, wherein the cable has segments extending from the tensioning mechanism and routed through the at least one cable guide to a bracket carried by the first strap.

6. The orthopedic device of claim 1, wherein the bracket defines a channel through which the cable extends transversely relative to a strap length to distribute tension across the width of the first strap when the first strap is tensioned.

7. The orthopedic device of claim 6, wherein a clamping tab connects the non-elastic segment to the elastic segment and bears a plurality of indicia.

8. The orthopedic device of claim 7, wherein a sleeve extends over the first shell and defines a slit through which the first strap extends, the clamping tab located proximate the slit and a border of the sleeve about the slit serves as an indicator for the indicia on the clamping tab.

9. The orthopedic device of claim 1, further comprising a second strap having a first end connected to the first shell by the cable such that the first and second straps are simultaneously adjustable by the tensioning mechanism.

10. The orthopedic device of claim 9, wherein the frame further comprises a second shell and a hinge connecting the first and second shells, second ends of the first and second straps securing to the second shell.

11. The orthopedic device of claim 10, wherein the first and second straps spiral between the first and second shells.

12. The orthopedic device of claim 10, wherein the second end of the first and second straps each include a bracket removably coupling to the second shell by an opening formed thereby.

13. The orthopedic device of claim 10, further comprising a stability strap circumferentially extending about a lower portion of the device in combination with the second shell, the stability strap has a first end carrying a fastener tab engageable with an opening formed by the second shell.

14. An orthopedic device, comprising:
a frame including a first shell;
a first strap having a first end carrying a bracket and connected to the first shell by a cable;
a tensioning mechanism connected to the cable and arranged to provide incremental adjustment of the cable among a plurality of predetermined settings, the tensioning mechanism being mounted directly onto the first shell;
at least one guide secured onto the first shell, the cable extending through the at least one guide between the tensioning mechanism and the first strap;
wherein the first strap includes a non-elastic segment and an elastic segment at the first end thereof carrying the bracket coupling to the cable.

15. The orthopedic device of claim 14, wherein the tensioning mechanism includes a knob, the orthopedic device further comprising a sleeve extending over the first shell and the knob protruding outwardly from the orthopedic device and outside the sleeve.

16. The orthopedic device of claim 14, wherein a clamping tab connects the non-elastic segment to the elastic segment and bears a plurality of indicia.

* * * * *